US010595737B2

(12) United States Patent
Korzinov et al.

(10) Patent No.: US 10,595,737 B2
(45) Date of Patent: Mar. 24, 2020

(54) SYSTEMS AND METHODS FOR CLASSIFYING ECG DATA

(71) Applicant: InfoBionic, Inc., Lowell, MA (US)

(72) Inventors: Lev Korzinov, San Diego, CA (US);
Eric Baumann, San Diego, CA (US);
Anna McNamara, Susquehanna, PA (US)

(73) Assignee: InfoBionic, Inc., Lowell, MA (US)

( * ) Notice: Subject to any disclaimer, the term of this patent is extended or adjusted under 35 U.S.C. 154(b) by 157 days.

(21) Appl. No.: 15/953,996

(22) Filed: Apr. 16, 2018

(65) Prior Publication Data

US 2018/0228390 A1 Aug. 16, 2018

Related U.S. Application Data

(63) Continuation of application No. 15/143,016, filed on Apr. 29, 2016, now Pat. No. 9,968,274.

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0006* (2013.01); *A61B 5/0022* (2013.01);
(Continued)

(58) Field of Classification Search
CPC ... A61B 5/04012; A61B 5/0006; A61B 5/022; A61B 5/0408; A61B 5/0468;
(Continued)

(56) References Cited

U.S. PATENT DOCUMENTS 3,832,994 A 9/1974 Bicher et al.
4,173,971 A 11/1979 Karz
(Continued)

FOREIGN PATENT DOCUMENTS

EP 0 959 607 A2 11/1999
WO WO 01/93756 A2 12/2001
(Continued)

OTHER PUBLICATIONS

International Search Authority, International Search Report and the Written Opinion for International Application No. PCT/US2012/033554 dated Aug. 28, 2012 (15 pages).
(Continued)

*Primary Examiner* — Lindsey G Wehrheim
(74) *Attorney, Agent, or Firm* — Bookoff McAndrews, PLLC

(57) ABSTRACT

A computer-implemented method for processing ECG data may include: receiving, over an electronic network, ECG data, wherein the ECG data represents a plurality of heartbeats; analyzing the ECG data, by at least one processor, to determine whether each of the plurality of heartbeats is a normal heartbeat or an abnormal heartbeat; associating, by the at least one processor, each of the abnormal heartbeats with either only one of a plurality of existing templates or a new template; receiving, from a user, input related to each new template, wherein the input includes either: a) a confirmation that the new template represents an abnormal heartbeat, or b) a reclassification of the new template as representing a normal heartbeat or a different abnormal heartbeat; and in response to the user input, updating, by the at least one processor, a label of each of the heartbeats associated with each confirmed new template and each of the heartbeats associated with each reclassified new tem-
(Continued)

plate. The ECG data may be received from a portable monitor configured to be carried on a patient's body.

20 Claims, 3 Drawing Sheets

(51) Int. Cl.
*A61B 5/0468* (2006.01)
*H04W 4/70* (2018.01)
*A61B 5/0408* (2006.01)
*H04B 1/3827* (2015.01)
*H04L 12/26* (2006.01)
*A61B 5/024* (2006.01)

(52) U.S. Cl.
CPC .......... *A61B 5/0408* (2013.01); *A61B 5/0468* (2013.01); *A61B 5/7246* (2013.01); *A61B 5/7264* (2013.01); *A61B 5/7475* (2013.01); *H04B 1/385* (2013.01); *H04L 43/04* (2013.01); *H04W 4/70* (2018.02); *A61B 5/02405* (2013.01); *A61B 5/02438* (2013.01); *A61B 5/04085* (2013.01); *A61B 5/6801* (2013.01); *A61B 5/7203* (2013.01); *A61B 5/7282* (2013.01); *A61B 2560/0431* (2013.01)

(58) Field of Classification Search
CPC ... A61B 5/7246; A61B 5/7264; A61B 5/7475; A61B 5/02405; A61B 5/02438; A61B 5/04085; A61B 5/6801; A61B 5/7203; A61B 5/7282; A61B 2560/0431; H04W 4/70; H04B 1/385; H04L 43/04
See application file for complete search history.

(56) References Cited

U.S. PATENT DOCUMENTS

| | | |
|---|---|---|
| 4,336,810 A | 6/1982 | Anderson et al. |
| 4,364,397 A | 12/1982 | Citron et al. |
| 4,635,646 A | 11/1987 | Gilles et al. |
| 4,721,114 A | 1/1988 | DuFault et al. |
| 4,791,933 A | 12/1988 | Asai et al. |
| 4,883,064 A | 11/1989 | Olson et al. |
| 4,905,205 A | 2/1990 | Rialan |
| 4,920,489 A | 4/1990 | Hubelbank et al. |
| 5,025,795 A | 6/1991 | Kunig |
| 5,058,597 A | 10/1991 | Onoda et al. |
| 5,080,105 A | 1/1992 | Thornton |
| 5,090,418 A | 2/1992 | Squires et al. |
| 5,226,431 A | 7/1993 | Bible et al. |
| 5,238,001 A | 8/1993 | Gallant et al. |
| 5,309,920 A | 5/1994 | Gallant et al. |
| 5,365,935 A | 11/1994 | Righter et al. |
| 5,398,183 A | 3/1995 | Gordon et al. |
| 5,417,222 A | 5/1995 | Dempsey et al. |
| 5,501,229 A | 3/1996 | Selker et al. |
| 5,502,688 A | 3/1996 | Recchione et al. |
| 5,544,661 A | 8/1996 | Davis et al. |
| 5,564,429 A | 10/1996 | Bornn et al. |
| 5,678,562 A | 10/1997 | Sellers |
| 5,718,233 A | 2/1998 | Selker et al. |
| 5,748,103 A | 5/1998 | Flach et al. |
| 5,782,773 A | 7/1998 | Kuo et al. |
| 5,871,451 A | 2/1999 | Unger et al. |
| 5,876,351 A | 3/1999 | Rohde |
| 5,944,659 A | 8/1999 | Flach et al. |
| 6,049,730 A | 4/2000 | Kristbjarnarson |
| 6,168,563 B1 | 1/2001 | Brown |
| 6,213,942 B1 | 4/2001 | Flach et al. |
| 6,225,901 B1 | 5/2001 | Kail, IV |
| 6,238,338 B1 | 5/2001 | DeLuca et al. |
| 6,272,377 B1 | 8/2001 | Sweeney et al. |
| 6,280,380 B1 | 8/2001 | Bardy |
| 6,366,871 B1 | 4/2002 | Geva |
| 6,389,308 B1 | 5/2002 | Shusterman |
| 6,411,840 B1 | 6/2002 | Bardy |
| 6,416,471 B1 | 7/2002 | Kumar et al. |
| 6,418,340 B1 | 7/2002 | Conley et al. |
| 6,441,747 B1 | 8/2002 | Khair et al. |
| 6,466,806 B1 | 10/2002 | Geva et al. |
| 6,471,087 B1 | 10/2002 | Shusterman |
| 6,485,418 B2 | 11/2002 | Yasushi et al. |
| 6,494,731 B1 | 12/2002 | Lovett |
| 6,494,829 B1 | 12/2002 | New, Jr. et al. |
| 6,496,705 B1 | 12/2002 | Ng et al. |
| 6,496,829 B1 | 12/2002 | New, Jr. et al. |
| 6,553,262 B1 | 4/2003 | Lang et al. |
| 6,569,095 B2 | 5/2003 | Eggers |
| 6,589,170 B1 | 7/2003 | Flach et al. |
| 6,602,191 B2 | 8/2003 | Quy |
| 6,611,705 B2 | 8/2003 | Hopman et al. |
| 6,648,820 B1 | 11/2003 | Sarel |
| 6,654,631 B1 | 11/2003 | Sahai |
| 6,664,893 B1 | 12/2003 | Eveland et al. |
| 6,665,385 B2 | 12/2003 | Rogers et al. |
| 6,694,177 B2 | 2/2004 | Eggers et al. |
| 6,694,186 B2 | 2/2004 | Bardy |
| 6,704,595 B2 | 3/2004 | Bardy |
| 6,708,057 B2 | 3/2004 | Morganroth |
| 6,773,396 B2 | 8/2004 | Flach et al. |
| 6,801,137 B2 | 10/2004 | Eggers |
| 6,804,558 B2 | 10/2004 | Haller et al. |
| 6,826,425 B2 | 11/2004 | Bardy |
| 6,840,904 B2 | 1/2005 | Goldberg |
| 6,856,832 B1 | 2/2005 | Matsumura et al. |
| 6,871,089 B2 | 3/2005 | Korzinov et al. |
| 6,897,788 B2 | 5/2005 | Khair et al. |
| 6,913,577 B2 | 7/2005 | Bardy |
| 6,925,324 B2 | 8/2005 | Shusterman |
| 6,940,403 B2 | 9/2005 | Kail, IV |
| 6,945,934 B2 | 9/2005 | Bardy |
| 6,957,107 B2 | 10/2005 | Rogers et al. |
| 6,980,112 B2 | 12/2005 | Nee |
| 6,987,965 B2 | 1/2006 | Ng et al. |
| 7,002,468 B2 | 2/2006 | Eveland et al. |
| 7,016,721 B2 | 3/2006 | Lee et al. |
| 7,058,444 B2 | 6/2006 | Logan et al. |
| 7,082,334 B2 | 7/2006 | Boute et al. |
| 7,092,751 B2 | 8/2006 | Erkkila |
| 7,099,715 B2 | 8/2006 | Korzinov et al. |
| 7,117,037 B2 | 10/2006 | Heibert et al. |
| 7,120,485 B2 | 10/2006 | Glass et al. |
| 7,130,396 B2 | 10/2006 | Rogers et al. |
| 7,156,809 B2 | 1/2007 | Quy |
| 7,171,166 B2 | 1/2007 | Ng et al. |
| 7,194,300 B2 | 3/2007 | Korzinov |
| 7,197,357 B2 | 3/2007 | Istvan et al. |
| 7,212,850 B2 | 5/2007 | Prystowsky et al. |
| 7,222,054 B2 | 5/2007 | Geva |
| 7,248,916 B2 | 7/2007 | Bardy |
| 7,257,438 B2 | 8/2007 | Kinast |
| 7,343,197 B2 | 3/2008 | Shusterman |
| 7,382,247 B2 | 6/2008 | Welch et al. |
| 7,403,808 B2 | 7/2008 | Istvan et al. |
| 7,412,281 B2 | 8/2008 | Shen et al. |
| 7,433,731 B2 | 10/2008 | Matsumara et al. |
| 7,477,933 B2 | 1/2009 | Ueyama |
| 7,509,160 B2 | 3/2009 | Bischoff et al. |
| 7,539,533 B2 | 5/2009 | Tran |
| 7,542,878 B2 | 6/2009 | Nanikashvili |
| 7,552,035 B2 | 6/2009 | Cataltepe et al. |
| 7,558,623 B2 | 7/2009 | Fischell et al. |
| 7,580,755 B1 | 8/2009 | Schwartz et al. |
| 7,587,237 B2 | 9/2009 | Korzinov et al. |
| 7,593,764 B2 | 9/2009 | Kohls et al. |
| 7,596,405 B2 | 9/2009 | Kurzweil et al. |
| 7,630,756 B2 | 12/2009 | Linker |
| 7,654,965 B2 | 2/2010 | Morganroth |
| 7,689,439 B2 | 3/2010 | Parker |
| 7,702,382 B2 | 4/2010 | Xue et al. |
| 7,706,883 B1 | 4/2010 | Sing |
| 7,715,905 B2 | 5/2010 | Kurzweil et al. |

(56) References Cited

U.S. PATENT DOCUMENTS

| | | |
|---|---|---|
| 7,729,753 B2 | 6/2010 | Kremliovsky et al. |
| 7,734,335 B2 | 6/2010 | Kontothanassis et al. |
| 7,761,143 B2 | 7/2010 | Matsumura et al. |
| D621,048 S | 8/2010 | Severe et al. |
| 7,783,342 B2 | 8/2010 | Syeda-Mahmood et al. |
| 7,801,591 B1 | 9/2010 | Shusterman |
| 7,803,118 B2 | 9/2010 | Reisfeld et al. |
| 7,803,119 B2 | 9/2010 | Reisfeld |
| 7,837,629 B2 | 11/2010 | Bardy |
| 7,844,323 B2 | 11/2010 | Fischell et al. |
| 7,860,557 B2 | 12/2010 | Istvan et al. |
| 7,907,996 B2 | 3/2011 | Prystowsky et al. |
| 7,912,537 B2 | 3/2011 | Lee et al. |
| 7,933,642 B2 | 4/2011 | Istvan et al. |
| 7,941,207 B2 | 5/2011 | Korzinov |
| 7,979,111 B2 | 7/2011 | Acquista |
| 7,996,075 B2 | 8/2011 | Korzinov et al. |
| 7,996,187 B2 | 8/2011 | Nanikashvili et al. |
| 8,005,531 B2 | 8/2011 | Xue et al. |
| 8,046,060 B2 | 10/2011 | Simms, Jr. |
| RE42,934 E | 11/2011 | Thompson |
| 8,055,332 B2 | 11/2011 | McCabe et al. |
| 8,064,990 B2 | 11/2011 | Diem et al. |
| 8,073,536 B2 | 12/2011 | Gunderson et al. |
| 8,121,673 B2 | 2/2012 | Tran |
| 8,126,728 B2 | 2/2012 | Dicks et al. |
| 8,126,729 B2 | 2/2012 | Dicks et al. |
| 8,126,730 B2 | 2/2012 | Dicks et al. |
| 8,126,732 B2 | 2/2012 | Dicks et al. |
| 8,126,733 B2 | 2/2012 | Dicks et al. |
| 8,126,734 B2 | 2/2012 | Dicks et al. |
| 8,126,735 B2 | 2/2012 | Dicks et al. |
| 8,150,502 B2 | 4/2012 | Kumar et al. |
| 8,160,682 B2 | 4/2012 | Kumar et al. |
| 8,190,246 B2 | 5/2012 | Belalcazar et al. |
| 8,204,580 B2 | 6/2012 | Kurzweil et al. |
| 8,224,430 B2 | 7/2012 | Fischell et al. |
| 8,225,238 B2 | 7/2012 | Wolk et al. |
| 8,244,335 B2 | 8/2012 | Kumar et al. |
| 8,255,041 B2 | 8/2012 | Istvan et al. |
| 8,255,238 B2 | 8/2012 | Powell et al. |
| 8,260,408 B2 | 9/2012 | Ostrow |
| 8,290,129 B2 | 10/2012 | Rogers et al. |
| 8,301,236 B2 | 10/2012 | Baumann et al. |
| 8,301,252 B2 | 10/2012 | Hatlestad et al. |
| 8,308,650 B2 | 11/2012 | Bardy |
| 8,323,188 B2 | 12/2012 | Tran |
| 8,326,407 B2 | 12/2012 | Linker |
| 8,328,718 B2 | 12/2012 | Tran |
| 8,352,018 B2 | 1/2013 | Xue et al. |
| 8,391,962 B2 | 3/2013 | Watanabe |
| 8,391,989 B2 | 3/2013 | Hatlestad et al. |
| 8,396,542 B2 | 3/2013 | Johnson et al. |
| 8,406,862 B2 | 3/2013 | Hopenfeld |
| 8,425,414 B2 | 4/2013 | Eveland |
| 8,425,415 B2 | 4/2013 | Tran |
| 8,428,703 B2 | 4/2013 | Hopenfeld |
| 8,428,705 B2 | 4/2013 | Kurzweil et al. |
| 8,449,471 B2 | 5/2013 | Tran |
| 8,478,389 B1 | 7/2013 | Brockway et al. |
| 8,478,418 B2 | 7/2013 | Fahey |
| 8,483,807 B2 | 7/2013 | Kurzweil et al. |
| 8,509,882 B2 | 8/2013 | Albert et al. |
| 8,535,223 B2 | 9/2013 | Corroy et al. |
| 8,606,351 B2 | 12/2013 | Wheeler |
| 8,620,418 B1 | 12/2013 | Kuppuraj et al. |
| 8,652,038 B2 | 2/2014 | Tran et al. |
| 8,655,441 B2 | 2/2014 | Fletcher et al. |
| 8,657,742 B2 | 2/2014 | Neumann |
| 9,968,274 B2 * | 5/2018 | Korzinov ............... H04W 4/70 |
| 2001/0023360 A1 | 9/2001 | Nelson et al. |
| 2001/0047127 A1 | 11/2001 | New et al. |
| 2002/0082665 A1 | 6/2002 | Haller et al. |
| 2002/0143576 A1 | 10/2002 | Nolvak et al. |
| 2002/0156384 A1 | 10/2002 | Eggers et al. |
| 2003/0028442 A1 | 2/2003 | Wagstaff et al. |
| 2003/0122677 A1 | 7/2003 | Kail, IV |
| 2003/0172940 A1 | 9/2003 | Rogers et al. |
| 2004/0006278 A1 | 1/2004 | Webb et al. |
| 2004/0100376 A1 | 5/2004 | Lye et al. |
| 2004/0127802 A1 | 7/2004 | Istvan et al. |
| 2004/0172290 A1 | 9/2004 | Leven |
| 2004/0260189 A1 | 12/2004 | Eggers et al. |
| 2005/0004486 A1 | 1/2005 | Glass et al. |
| 2005/0049515 A1 | 3/2005 | Misczynski et al. |
| 2005/0101875 A1 | 5/2005 | Semler et al. |
| 2005/0131308 A1 | 6/2005 | Chio et al. |
| 2005/0154325 A1 | 7/2005 | Lauter et al. |
| 2005/0165318 A1 | 7/2005 | Brodnick et al. |
| 2005/0182308 A1 | 8/2005 | Bardy |
| 2005/0182334 A1 | 8/2005 | Korzinov et al. |
| 2005/0203349 A1 | 9/2005 | Nanikashvili |
| 2005/0234307 A1 | 10/2005 | Heinonen et al. |
| 2006/0079797 A1 | 4/2006 | Bischoff et al. |
| 2006/0079798 A1 | 4/2006 | Bischoff et al. |
| 2006/0149156 A1 | 7/2006 | Cochran et al. |
| 2006/0206066 A1 | 9/2006 | Ferek-Petric |
| 2006/0229522 A1 | 10/2006 | Barr |
| 2007/0010748 A1 | 1/2007 | Rauch et al. |
| 2007/0027388 A1 | 2/2007 | Chou |
| 2007/0073266 A1 | 3/2007 | Chmiel et al. |
| 2007/0093719 A1 | 4/2007 | Nichols et al. |
| 2007/0130657 A1 | 6/2007 | Rogers et al. |
| 2007/0179357 A1 | 8/2007 | Bardy |
| 2007/0179376 A1 | 8/2007 | Gerder |
| 2007/0191723 A1 | 8/2007 | Prystowsky |
| 2007/0197878 A1 | 8/2007 | Shklarski |
| 2007/0208233 A1 | 9/2007 | Kovacs |
| 2007/0270665 A1 | 11/2007 | Yang et al. |
| 2007/0276270 A1 | 11/2007 | Tran |
| 2007/0279217 A1 | 12/2007 | Venkatraman et al. |
| 2007/0279239 A1 | 12/2007 | Lachenit et al. |
| 2007/0293776 A1 | 12/2007 | Korzinov et al. |
| 2008/0004904 A1 | 1/2008 | Tran |
| 2008/0071182 A1 * | 3/2008 | Cazares ............... A61B 5/0464 600/509 |
| 2008/0097550 A1 | 4/2008 | Dicks et al. |
| 2008/0097551 A1 | 4/2008 | Dicks et al. |
| 2008/0097552 A1 | 4/2008 | Dicks et al. |
| 2008/0097793 A1 | 4/2008 | Dicks et al. |
| 2008/0097908 A1 | 4/2008 | Dicks et al. |
| 2008/0097909 A1 | 4/2008 | Dicks et al. |
| 2008/0097910 A1 | 4/2008 | Dicks et al. |
| 2008/0097911 A1 | 4/2008 | Dicks et al. |
| 2008/0097912 A1 | 4/2008 | Dicks et al. |
| 2008/0097913 A1 | 4/2008 | Dicks et al. |
| 2008/0097914 A1 | 4/2008 | Dicks et al. |
| 2008/0097917 A1 | 4/2008 | Dicks et al. |
| 2008/0103370 A1 | 5/2008 | Dicks et al. |
| 2008/0103554 A1 | 5/2008 | Dicks et al. |
| 2008/0103555 A1 | 5/2008 | Dicks et al. |
| 2008/0108907 A1 | 5/2008 | Stahmann et al. |
| 2008/0125824 A1 * | 5/2008 | Sauer ................... A61N 1/3622 607/14 |
| 2008/0139894 A1 | 6/2008 | Szydlo-Moore et al. |
| 2008/0183502 A1 | 7/2008 | Dicks et al. |
| 2008/0215120 A1 | 9/2008 | Dicks et al. |
| 2008/0215360 A1 | 9/2008 | Dicks et al. |
| 2008/0218376 A1 | 9/2008 | Dicks et al. |
| 2008/0224852 A1 | 9/2008 | Dicks et al. |
| 2008/0281215 A1 | 11/2008 | Alhussiny |
| 2009/0076344 A1 | 3/2009 | Libbus et al. |
| 2009/0076345 A1 | 3/2009 | Manicka et al. |
| 2009/0076350 A1 | 3/2009 | Bly et al. |
| 2009/0076405 A1 | 3/2009 | Amurthur et al. |
| 2009/0099469 A1 | 4/2009 | Flores |
| 2009/0112769 A1 | 4/2009 | Dicks et al. |
| 2009/0115628 A1 | 5/2009 | Dicks et al. |
| 2009/0124869 A1 | 5/2009 | Hu et al. |
| 2009/0149718 A1 | 6/2009 | Kim et al. |
| 2009/0171227 A1 | 7/2009 | Dziubinski et al. |
| 2009/0234672 A1 | 9/2009 | Dicks et al. |
| 2009/0261968 A1 | 10/2009 | El-Hamamsy et al. |
| 2009/0264783 A1 | 10/2009 | Xi et al. |

(56) References Cited

U.S. PATENT DOCUMENTS

| | | | |
|---|---|---|---|
| 2009/0275854 A1 | 11/2009 | Zielinski et al. |
| 2009/0299207 A1 | 12/2009 | Barr |
| 2009/0326981 A1 | 12/2009 | Karkanias et al. |
| 2010/0049006 A1 | 2/2010 | Magar et al. |
| 2010/0056881 A1 | 3/2010 | Libbus et al. |
| 2010/0069735 A1 | 3/2010 | Berkner |
| 2010/0076325 A1 | 3/2010 | Cho et al. |
| 2010/0113895 A1 | 5/2010 | Cho et al. |
| 2010/0160742 A1 | 6/2010 | Seidl et al. |
| 2010/0198089 A1 | 8/2010 | Litovchick et al. |
| 2010/0204586 A1 | 8/2010 | Pu et al. |
| 2010/0249541 A1 | 9/2010 | Geva et al. |
| 2010/0249625 A1 | 9/2010 | Lin |
| 2010/0250271 A1 | 9/2010 | Pearce et al. |
| 2010/0268103 A1 | 10/2010 | McNamara et al. |
| 2010/0286545 A1 | 11/2010 | Wolfe et al. |
| 2010/0298664 A1 | 11/2010 | Baumann et al. |
| 2010/0331649 A1 | 12/2010 | Chou |
| 2011/0004072 A1 | 1/2011 | Fletcher et al. |
| 2011/0009711 A1 | 1/2011 | Nanikashvili |
| 2011/0066042 A1 | 3/2011 | Pandia et al. |
| 2011/0066555 A1 | 3/2011 | Dicks et al. |
| 2011/0071364 A1 | 3/2011 | Kuo et al. |
| 2011/0078441 A1 | 3/2011 | Dicks et al. |
| 2011/0090086 A1 | 4/2011 | Dicks et al. |
| 2011/0092835 A1 | 4/2011 | Istvan et al. |
| 2011/0093283 A1 | 4/2011 | Dicks et al. |
| 2011/0093284 A1 | 4/2011 | Dicks et al. |
| 2011/0093285 A1 | 4/2011 | Dicks et al. |
| 2011/0093286 A1 | 4/2011 | Dicks et al. |
| 2011/0093287 A1 | 4/2011 | Dicks et al. |
| 2011/0093297 A1 | 4/2011 | Dicks et al. |
| 2011/0097710 A1 | 4/2011 | Macrae et al. |
| 2011/0098583 A1 | 4/2011 | Pandia et al. |
| 2011/0105928 A1 | 5/2011 | Bojovic et al. |
| 2011/0137133 A1 | 6/2011 | Espina |
| 2011/0144470 A1 | 6/2011 | Mazar et al. |
| 2011/0158430 A1 | 6/2011 | Dicks et al. |
| 2011/0161111 A1 | 6/2011 | Dicks et al. |
| 2011/0166466 A1 | 7/2011 | Chon et al. |
| 2011/0166468 A1 | 7/2011 | Prystowsky et al. |
| 2011/0167250 A1 | 7/2011 | Dicks et al. |
| 2011/0179405 A1 | 7/2011 | Dicks et al. |
| 2011/0245633 A1 | 10/2011 | Goldberg et al. |
| 2011/0270049 A1 | 11/2011 | Katra et al. |
| 2011/0270112 A1 | 11/2011 | Manera et al. |
| 2011/0288379 A1 | 11/2011 | Wu |
| 2011/0301435 A1 | 12/2011 | Albert et al. |
| 2011/0301439 A1 | 12/2011 | Albert et al. |
| 2012/0022387 A1 | 1/2012 | Balda |
| 2012/0101396 A1 | 4/2012 | Solosko et al. |
| 2012/0165616 A1 | 6/2012 | Geva et al. |
| 2012/0179055 A1 | 7/2012 | Tamil et al. |
| 2012/0203124 A1 | 8/2012 | Lim |
| 2012/0215123 A1 | 8/2012 | Kumar et al. |
| 2013/0085364 A1 | 4/2013 | Lu et al. |
| 2013/0109927 A1 | 5/2013 | Menzel |
| 2013/0197322 A1 | 8/2013 | Tran |
| 2013/0204100 A1 | 8/2013 | Acquista |
| 2013/0225967 A1 | 8/2013 | Esposito |
| 2013/0237861 A1 | 9/2013 | Margarida et al. |
| 2013/0237874 A1 | 9/2013 | Zoicas |
| 2013/0245387 A1 | 9/2013 | Patel |
| 2013/0245472 A1 | 9/2013 | Eveland |
| 2013/0253354 A1 | 9/2013 | Fahey |
| 2013/0253355 A1 | 9/2013 | Fahey |
| 2013/0289424 A1 | 10/2013 | Brockway et al. |
| 2013/0303926 A1 | 11/2013 | Kurzweil et al. |
| 2013/0331663 A1 | 12/2013 | Albert et al. |
| 2013/0338516 A1 | 12/2013 | Manera et al. |
| 2013/0338518 A1 | 12/2013 | Zoica |
| 2014/0081162 A1 | 3/2014 | Snell et al. |

FOREIGN PATENT DOCUMENTS

| | | |
|---|---|---|
| WO | WO 01/93756 A3 | 12/2001 |
| WO | WO 02/082799 A2 | 10/2002 |
| WO | WO 02/082799 A3 | 10/2002 |
| WO | WO 2011/080189 A1 | 7/2011 |
| WO | WO 2016/028888 A1 | 2/2016 |

OTHER PUBLICATIONS

International Search Authority, International Search Report and the Written Opinion for International Application No. PCT/US2012/033592 dated Aug. 31, 2012 (14 pages).

Jovanov et al., "Patient Monitoring Using Personal Area Networks of Wireless Intelligent Sensors," Electrical and Computer Engineering Department, University of Alabama in Huntsville, Biomedical Sciences Instrumentation, 37:378-8, 6 pages, 2001.

Hopley et al., "The Magnificent ROC (Receiver Operating Characteristic Curve)," http://www.anaestheist.com/stats/roc/index.htm, 26 pages, Sep. 21, 2001.

Chazal et al., "Automatic Classification of Heartbeats Using ECG Morphology and Heartbeat Interval Features," IEEE Transactions on Biomedical Engineering, vol. 51, No. 7, pp. 1196-1206, 11 pages, Jul. 2004.

Philips, "Philips Remote Patient Monitoring," Philips Medical Systems, 4 pages, 2007.

Archive.org, "Clinical Policy Bulletin: Cardiac Event Monitors," No. 0073, Aetna, Inc., web.archive.org_web_20090514063858_http_www.aetna.com_cpb_medical_data_1_99_0073.html, 10 pages, May 14, 2009.

Center for Technology and Aging, "Technologies for Remote Patient Monitoring in Older Adults," Center for Technology and Aging, Position Paper, Discussion Draft, 30 pages, Dec. 2009.

Edevice, "M2M Solutions for Home Health Monitoring," edevice, http://www.edevice.com/medical/?gclid=CPCdlfiR_KcCFUpN4AodZEyzqO, 2 pages, 2010.

MedApps, Inc., "MedApps Mobile Wireless Remote Patient Monitoring" http://www.medapps.com/, 3 pages, 2010.

Archive.org, "The Area Under an ROC Curve," http://web.archive.org/web/20100527211847/http://gim.unmc.edu/dxtests/roc3.htm, 2 pages, May 27, 2010.

Medical Biostatistics.com, "Sensitivity-Specificity, Bayes' Rule, and Predictives," MedicalBiostatistics.com, http://www.medicalbiostatistics.com/ROCCurve.pdf, 4 pages, Sep. 5, 2010.

Medical Biostatistics.com, "ROC Curve," MedicalBiostatistics.com, 9 pages, Sep. 25, 2010.

IEEE, "Remote Patient Monitoring Service Using Heterogeneous Wireless Access Networks: Architecture and Optimization" Niyato et al. paper abstract, IEEE Xplore Digital Library http://ieeexplore.ieee.org/xpl/freeabs_all.jsp?arnumber=4909280, 1 page, 2011.

TriMed Media Group, Inc., "FDA Green Lights AirStrip Smartphone Patient Monitoring Tool," TriMed Media Group, Inc., http://cardiovascularbusiness.com/index.php?option=com_articles&article=23414&publication=137&view=portals&form=article23414&limitstart=30, 1 page, 2011.

Google Patents, Google Patent Search: "Healthcare Monitoring "web server" smartphone or mobile," www.google.com/patents, Mar. 9, 2011, 2 pages.

Wikipedia.org, "Holter Monitor," Wikipedia.org, http://en.wikipedia.org/w/index.php?title=Holter_monitor&oldid=417997699, Mar. 9, 2011, 4 pages.

Aetna, Inc., "Clinical Policy Bulletin: Cardiac Event Monitors," No. 0073, Aetna, Inc., www.aetna.com_cpb_medical_data_1_99_0073.html, 10 pages, Mar. 11, 2011.

Wikipedia.org, "Receiver Operating Characteristics," Wikipedia.org, http://en.wikipedia.org/wiki/Receiver_operating_characteristic, 6 pages, Apr. 14, 2011.

Medical Biostatistics.com, "Predictives Based ROC Curve," MedicalBiostatistics.com http://www.medicalbiostatistics.com/PredictivityBasedROC.pdf, 3 pages, Sep. 5, 2012.

International Preliminary Report on Patentability, PCT/US2012/033554; dated Oct. 15, 2013.

(56) References Cited

OTHER PUBLICATIONS

International Preliminary Report on Patentability; PCT/US2012/033592; dated Oct. 15, 2013.
International Search Report and the Written Opinion issued in related PCT/US2017/028798 dated Jul. 10, 2017 (14 pgs).

* cited by examiner

SYSTEMS AND METHODS FOR CLASSIFYING ECG DATA

This application is a continuation of U.S. application Ser. No. 15/143,016 filed on Apr. 29, 2016, which is incorporated by reference in its entirely herein.

TECHNICAL FIELD

Various embodiments of the present disclosure relate to a device and systems and methods of using the device for health monitoring, and more particularly to a device and system and methods of using a device for physiologic data monitoring.

BACKGROUND

Physiologic data may be used to monitor the health of a patient. For example, bioelectric signals (e.g., electrocardiogram or ECG signals) from the patient's heart may be used to monitor cardiac health. ECG is a recording of the electrical activity of the heart. During ECG monitoring, electrodes attached to a patient's skin are used to detect electrical activity of the heart over a period of time, and electrical impulses generated by the heart during each heartbeat are detected and recorded and/or displayed on a device. Analysis of the data reveals the cardiac health (e.g., rate and regularity of heartbeats, size and position of the chambers, the presence of any damage to the heart, effects of drugs or devices used to regulate the heart, etc.) of the patient.

Multiple electrodes (e.g., left arm (LA), right arm (RA), and left leg (LL) electrodes) may be attached to the patient's skin for ECG measurement. These electrodes may be combined into a number of pairs (e.g., three pairs LA-RA, LA-LL, and RA-LL), and voltage signals may be recorded across each pair. Each pair is known as a lead. Each lead looks at the heart from a different angle. Different types of ECG measurements can be referred to by the number of leads that are recorded (e.g., 3-lead, 5-lead, 12-lead ECG, etc.).

Many cardiac problems become noticeable only during physical activity (walking, exercise, etc.). An ambulatory electrocardiogram (ECG) continuously monitors the electrical activity of the heart while a patient does normal activities. Typically, a 12-lead or a 5-lead ECG is used for periodic ECG monitoring (e.g., at a doctor's office, etc.) and a 3-lead ECG is used for continuous ambulatory monitoring. In 3-lead monitoring, ECG data is collected using three electrodes attached to the patient. The collected data is recorded in a monitor operatively coupled to the electrodes. The stored data is analyzed by a health care provider. In some cases, the monitor may transmit ECG data to a health care provider for analysis. Several types of monitors (e.g., Holter monitor, event monitors, mobile cardiovascular telemetry monitors, etc.) are known in the art. Some of these monitors store the data for subsequent analysis by a health care provider, while others transmit (real-time, periodically, or on demand) the collected ECG data to a remote site where it is analyzed.

SUMMARY

Embodiments of the present disclosure relate to, among other things, devices for physiologic data monitoring. Each of the embodiments disclosed herein may include one or more of the features described in connection with any of the other disclosed embodiments.

A computer-implemented method for processing ECG data may include: receiving, over an electronic network, ECG data, wherein the ECG data represents a plurality of heartbeats; analyzing the ECG data, by at least one processor, to determine whether each of the plurality of heartbeats is a normal heartbeat or an abnormal heartbeat; associating, by the at least one processor, each of the abnormal heartbeats with either only one of a plurality of existing templates or a new template; receiving, from a user, input related to each new template, wherein the input includes either: a) a confirmation that the new template represents an abnormal heartbeat, or b) a reclassification of the new template as representing a normal heartbeat or a different abnormal heartbeat; and in response to the user input, updating, by the at least one processor, a label of each of the heartbeats associated with each confirmed new template and each of the heartbeats associated with each reclassified new template.

A system for processing ECG data may include a data storage device that stores instructions for processing ECG data; and a processor configured to execute the instructions to perform a method including: receiving, over an electronic network, ECG data, wherein the ECG data represents a plurality of heartbeats; analyzing the ECG data to determine whether each of the plurality of heartbeats is a normal heartbeat or an abnormal heartbeat; associating each of the abnormal heartbeats with either only one of a plurality of existing templates or a new template; receiving, from a user, input related to each new template, wherein the input includes either: a) a confirmation that the new template represents an abnormal heartbeat, or b) a reclassification of the new template as representing a normal heartbeat or a different abnormal heartbeat; and in response to the user input, updating the labels of each of the heartbeats associated with each confirmed new template and each of the heartbeats associated with each reclassified new template.

A non-transitory computer-readable medium may store instructions that, when executed by a computer, cause the computer to perform a method for processing ECG data, the method including: receiving, over an electronic network, ECG data, wherein the ECG data represents a plurality of heartbeats; analyzing the ECG data, by at least one processor, to determine whether each of the plurality of heartbeats is a normal heartbeat or an abnormal heartbeat; associating, by the at least one processor, each of the abnormal heartbeats with either only one of a plurality of existing templates or a new template; receiving, from a user, input related to each new template, wherein the input includes either: a) a confirmation that the new template represents an abnormal heartbeat, or b) a reclassification of the new template as representing a normal heartbeat or a different abnormal heartbeat; and in response to the user input, updating, by the at least one processor, a label of each of the heartbeats associated with each confirmed new template and each of the heartbeats associated with each reclassified new templates.

A method, system, or non-transitory computer-readable medium for processing ECG data may additionally or alternatively include one or more of the following steps or features: the method does not include repeating the analyzing step; the method may further comprise totaling, by the at least one processor, the number of heartbeats associated with the confirmed new templates and the number of heartbeats associated with the new templates reclassified as a different abnormal heartbeat; the associating step may include comparing ECG data representing a heartbeat to at least one of the plurality of existing templates; the step of associating may include creating the new template for abnormal heartbeats having characteristics that differ by more than a predefined threshold from each of the existing templates; the step of associating an abnormal heartbeat with one of the plurality of existing templates may include associating the abnormal heartbeat with an existing template if the abnormal heartbeat has characteristics that differ by less than a predefined threshold from the existing template; the abnormal heartbeats may include premature ventricular contractions; the electronic network may include a wireless connection over a cellular network; and the receiving step may include receiving the ECG data from a monitor, and the monitor may be a portable device configured to be carried on a patient's body.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DETAILED DESCRIPTION

Overview of a System for Monitoring Physiologic Data

Embodiments of the present disclosure may include methods and systems for monitoring physiologic data of a patient. Various aspects of the present disclosure may be used in combination with, or include, one or more features disclosed in U.S. Pat. No. 8,478,418 (issued Jul. 2, 2013) and U.S. Pat. No. 8,620,418 (issued Dec. 31, 2013), each of which is incorporated by reference herein in its entirety. While an exemplary embodiment of measuring ECG data is described below, it should be noted that the current disclosure may be applied to the measurement of any physiologic data. For example, the disclosed systems and methods may be used to measure signals indicative of heart rate, activity level (e.g., physical mobility or movement), respiration rate, blood pressure (e.g., systolic and/or diastolic), blood oxygen saturation (SpO2), blood glucose or insulin level, pulse oximetry, impedance, body temperature, etc. Thus, the systems, devices, and methods described herein may acquire and process other types of physiologic data instead of or in addition to ECG data. It is also contemplated that, in some embodiments, the measured physiologic data may be used to determine a cardiac safety indicator such as QT prolongation, ST elevation, etc.

Figure 1:
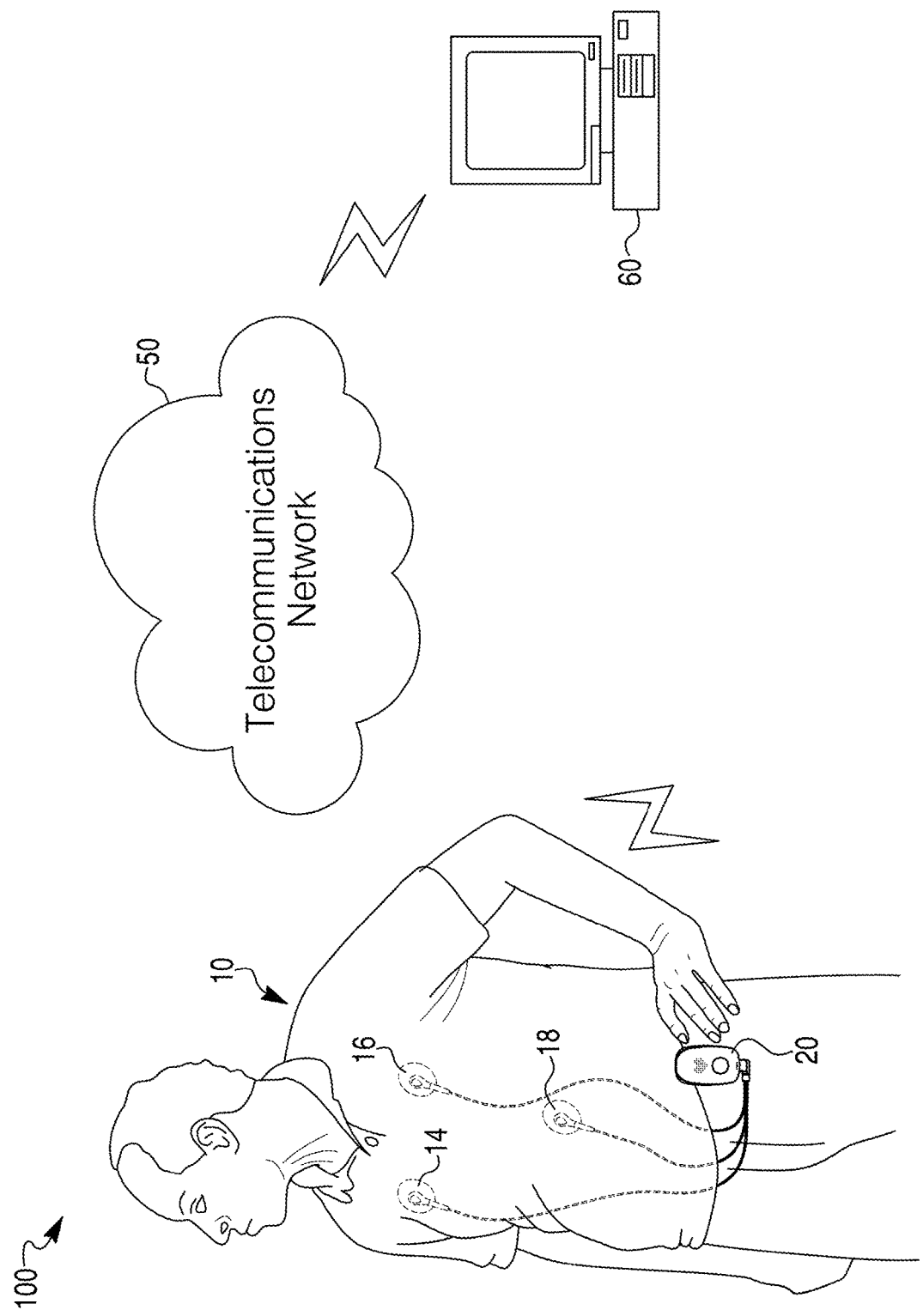
FIG. 1 illustrates an exemplary system for measuring ECG of a patient.

FIG. 1 is a schematic illustration of an exemplary system 100 for measuring ECG of a patient 10. A plurality of electrodes 14, 16, 18 may be attached to the patient 10 to detect ECG signals. Although a three-electrode configuration is illustrated, electrodes may be placed to measure any number of leads (e.g., a 10 electrode, 12-lead configuration). In one example, the electrodes 14, 16, 18 acquire two leads (channels) of ECG data. The electrodes 14, 16, 18 detect (and in some cases amplify) tiny electrical changes on the skin that are caused when heart muscles depolarize during each heartbeat. At rest, each heart muscle cell has a negative charge (called the membrane potential) across its cell membrane. Decreasing this negative charge toward zero, via the influx of the positive cations (Na+ and Ca++) is called depolarization. Depolarization activates mechanisms in the cell that cause it to contract. During each heartbeat, a healthy heart will have an orderly progression of a wave of depolarization that is triggered by the cells in the sinoatrial node, spreads out through the atrium, passes through the atrioventricular node and then spreads all over the ventricles. The depolarization wave (or ECG data) is indicative of the overall rhythm of the heart and is detected as variations in voltage between the electrode pairs (e.g., between electrodes 14-16, 14-18, and 16-18).

System 100 may include a monitor 20 operatively coupled to the electrodes 14, 16, 18. Monitor 20 may be adapted to receive and store the ECG data from the electrodes 14, 16, 18 using standard connections known in the art (e.g., lead wires, an analog to digital converter, etc.). In one example, the lead wires connected to each electrode in FIG. 1 may include a resistor. If a patient is undergoing defibrillation, the resistor may prevent the monitor from diverting energy applied to the patient by the defibrillation device. The presence of resistors in the lead wires does not inhibit impedance tomography. In one example, the resistor in each lead wire may be 1000 ohms.

In addition to the connection to electrodes 14, 16, 18, the monitor 20 may be configured to communicate with one or more additional or alternative sensors via wired or wireless connections. Any combination of well-known physiological sensors may be coupled to the monitor 20, such as SpO2 sensors, blood pressure sensors, heart electrodes (e.g., electrodes 14, 16, 18), respiration sensors, movement and activity sensors, glucose monitors, and the like. Respiration data may be derived from ECG baseline data, as is known to those of skill in the art. In one example, the monitor 20 can connect to a sensor in a scale to receive information related to the patient's weight. Movement or activity may be sensed with appropriate accelerometers or gyroscopes, which may include micro electro-mechanical system (MEMS) devices. The one or more additional or alternative sensors may be connected to the monitor 20 via wires or optical cables or via a wireless link (e.g., Bluetooth, Wi-Fi, ZigBee, Z-wave, radio, etc.).

In one example, at least one type of sensor transmits data to the monitor 20 via a wired connection, and at least one type of sensor transmits data to the monitor 20 via a wireless connection. The patient 10 may press a button on the monitor 20 to wirelessly pair it with one or more of the sensors described above. In another example, a user may communicate with a monitor 20 via a web/mobile interface component to wirelessly pair the monitor 20 with selected sensors.

In some embodiments, monitor 20 may transfer at least a portion of the measured ECG data (or other physiologic data) to a remote analysis station 60 for analysis. Although analysis station 60 is illustrated as a computer (e.g., processor and memory), in general, analysis station 60 may include any collection of computational devices (e.g., one or more servers, databases, and computers networked together) and personnel. The term "processor" as used herein may include a central processing unit or a microprocessor. The ECG data from monitor 20 may be transferred to remote analysis station 60 over a wired connection, using a portable storage medium (transferrable memory device, etc.), or wirelessly over a telecommunications network 50 (e.g., a cellular network, the Internet, a computer network, etc.). For example, monitor 20 may include a cellular modem, and the ECG data may be sent to the analysis station 60 via a cellular network. As used herein, the term "electronic network" may include any combination of wired and wireless communication technologies used to transmit information.

Analysis station 60 may analyze the ECG data to check the cardiac health of patient 10. Any analysis methodology known in the art may be used to analyze the received data (e.g., a methodology described by Philip de Chazal, et al., in "Automatic Classification of Heartbeats Using ECG Morphology and Heartbeat Interval Features," IEEE Transactions on Biomedical Engineering, Vol. 51, No. 7, July, 2004). In some embodiments, monitor 20 may at least partially analyze the collected ECG data before it is transferred to analysis station 60.

In some embodiments, monitor 20 may store the collected ECG data, and continuously transmit (directly or through an intermediate device) a subset of the data (e.g., data at a lower resolution, etc.) to the analysis station 60. In one example, the subset of the data is transmitted at 100 samples per second, although it may be transmitted at 200 samples per second or at any other frequency. The analysis station 60 may analyze the received data to determine if it indicates an anomaly (e.g., an arrhythmia, an unexpected trend in the data, etc.). If an anomaly is indicated, analysis station 60 may request (i.e. transmit instructions) the monitor 20 for more data (e.g., data from the same time frame at a higher resolution, etc.). For example, if the initial data was transmitted at 100 samples per second, the second set of more detailed data may be transmitted at 200 samples per second. Upon receipt of this request, the monitor 20 may retrieve the requested data from memory and transmit it to the analysis station 60. The analysis station 60 may then analyze the data (e.g., using a more rigorous analysis methodology) to confirm or refute the anomaly detected during the previous analysis. This analysis methodology is described in more detail in U.S. Pat. No. 8,478,418, which is incorporated by reference herein.

Monitor

Figure 2:
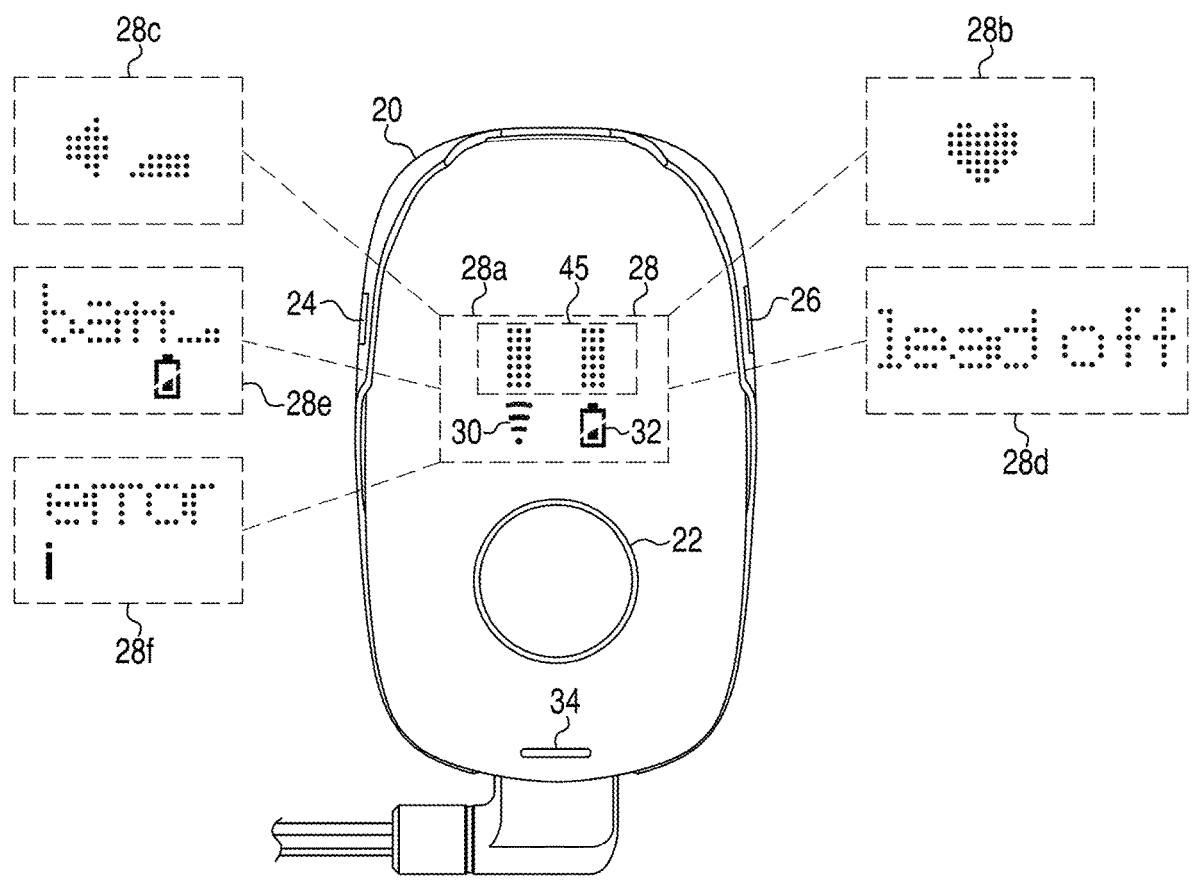
FIG. 2 illustrates an exemplary device used in the ECG measurement system of FIG. 1.

FIG. 2 illustrates an exemplary embodiment of monitor 20. Monitor 20 may include integrated circuits (microprocessor, memory, communication devices, etc.), visual displays (LED, LCD, etc.), and/or buttons that can be activated by the patient 10. The integrated circuits of monitor 20 may enable processing of collected ECG data, and communication between monitor 20 and the analysis station 60. The buttons may enable the patient 10 to trigger an activity (data collection, communication with analysis station 60, record or mark an event, etc.), and the display may enable the monitor 20 and analysis station 60 to communicate with patient 10 (e.g., using text messages). In one embodiment, the monitor 20 may include dimensions of approximately 108 mm×67 mm×17 mm, although the monitor 20 may be any size that allows it to be portable with the patient.

Monitor 20 may be a portable device, sized and adapted to be kept in the possession (strapped, attached, placed in the pocket, etc.) of patient 10. Such a portable monitor 20 may enable the patient 10 to go about the patient's daily activities while the monitor 20 records (and/or transfers, analyzes, etc.) ECG data. In the exemplary embodiment illustrated in FIG. 1, monitor 20 is shown as a device attached by a connector (e.g., clipped) to the patient's belt. However, this is only exemplary, and other configurations are possible (e.g., the connector could allow the device to be worn around the patient's neck). In embodiments where electrodes 14, 16, 18 are connected by a wire to the monitor, monitor 20 may include a connector to receive the connecting wire. In embodiments where electrodes 14, 16, 18 are coupled wirelessly, monitor 20 may include a transceiver to communicate with a transceiver of electrodes 14, 16, 18.

In one embodiment, the monitor 20 may include an event button 22, a wake button 24, and a volume button 26. A physician may press the event button 22 to activate the monitor 20 for patient use. Furthermore, the patient 10 may press the event button 22 if a symptom, such as the feeling caused by an arrhythmia, occurs. However, the monitor 20 may continuously record ECG data whether or not the patient presses the event button 22. Information from the event button 22 may therefore serve to help confirm suspected arrhythmias or other irregular heart activity detected from the ECG data. The wake button 24 may be pressed by the patient 10 to display the current level of reception (e.g., via a cellular network), the battery level, and/or whether the electrodes 14, 16, 18 are adequately coupled to the patient 10. Upon pressing the wake button 24, a light 34 may be green if the electrodes are all adequately coupled to the patient or red if one or more of the electrodes is not adequately coupled to the patient. The volume button 26 may allow the patient 10 to adjust or mute the volume of alerts from the monitor 20.

The monitor 20 may include a display 28. The display 28 may include a plurality of LED lights and one or more icons underneath the outer casing of the monitor. The LED lights may form an LED matrix 45 (e.g., 24×7, 20×7, or any other suitable arrangement of lights). In one embodiment, when the lights are off, the display is either imperceptible or faintly visible. When one or more LED lights or icons are lit, however, the individual lights or icons may be visible through the portion of the outer casing of the monitor that overlays the display 28. That portion of monitor 20 (a window over display 28) may be made of a transparent or semi-transparent material, for example, translucent polycarbonate.

A variety of display patterns may appear on the display 28 at various times to provide information to the patient 10. In FIG. 2, for example, the display pattern 28a may include a wireless icon 30 and a battery icon 32, which each correspond to one or more columns (e.g., three) of LED lights. Display pattern 28a may appear when the user (e.g., a physician, nurse, technician, patient, or any other person) presses the wake button 24. The columns of LED lights may indicate the level of wireless service and the battery level, respectively. Display pattern 28b may include an icon shaped like a heart, which may be displayed when the event button 22 is pressed. Display pattern 28c may include a speaker and rows of LED lights, and may be displayed when the user changes the volume. The number of rows of LED lights may increase when the volume is raised and decrease when the volume is lowered. "Mute" may be spelled in LED lights next to a speaker icon when the sound is muted. When one or more electrodes is not connected to the patient 10, the words "lead off" may scroll across the LED display, as shown in display pattern 28d. Alternatively, the words "lead" and "off" may alternate on the display 28. Display pattern 28e may appear when the battery is low. The number of rows of LED lights that appear may correspond to the level of battery remaining. Furthermore, the battery icon may appear red to indicate low battery status. In a final example, display pattern 28f may appear if there is an error that requires user attention. The LED lights may be lit in any suitable pattern or may form any words to communicate to the patient 10.

In other examples, display 28 may be separate from the monitor 20. The separate display 28 could be a stand-alone display or could be a user's cell phone or other communication device. The monitor 20 may transmit information to the stand-alone display, cell phone, or other communication device via any type of wireless network.

The monitor 20 may include a rechargeable battery. In one example, the battery may operate for between 24 and 72 hours on a single charge. The battery may be removable from the monitor 20 and docked to an external charger.

The hardware of monitor 20 may include various components connected by general purpose input/outputs or by specialized connectors. The hardware may include any suitable microprocessor and other circuitry known to one of ordinary skill in the art for performing the various functions of the system described herein, such as analog-to-digital converters, device/component drivers, tranceivers, and memory. The system software may receive ECG data for evaluation by an arrhythmia analysis algorithm, and any detected arrhythmias may be identified and presented for physician review. The system software may detect, for example, premature ventricular contractions (PVCs) from the ECG data, as will be described further below.

Method for Processing of ECG Data

Figure 3:
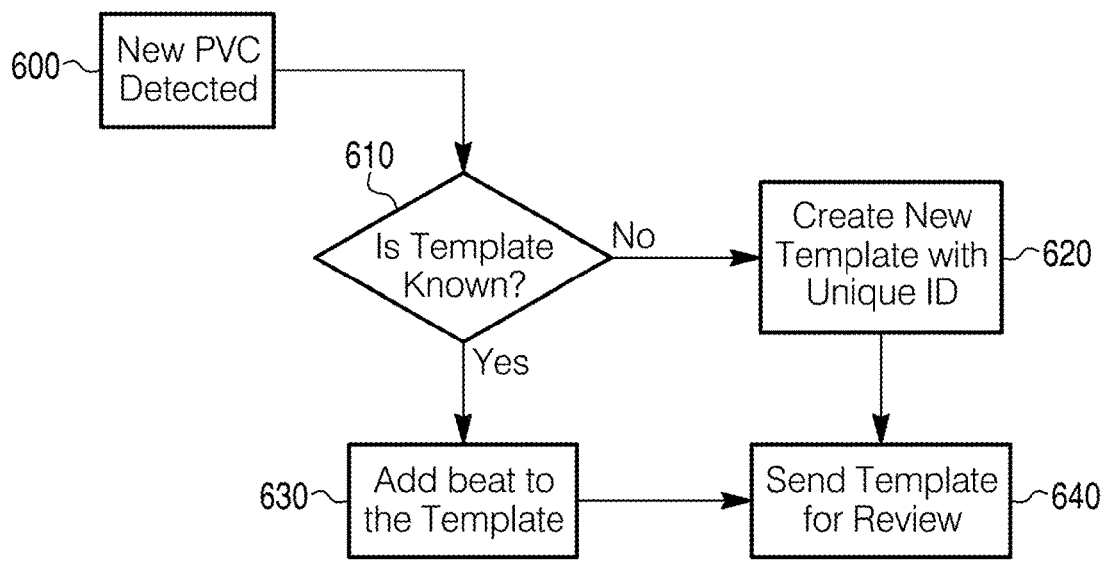
FIGS. 3 and 4 illustrate steps in an exemplary process for detecting and classifying arrhythmias.
Figure 4:
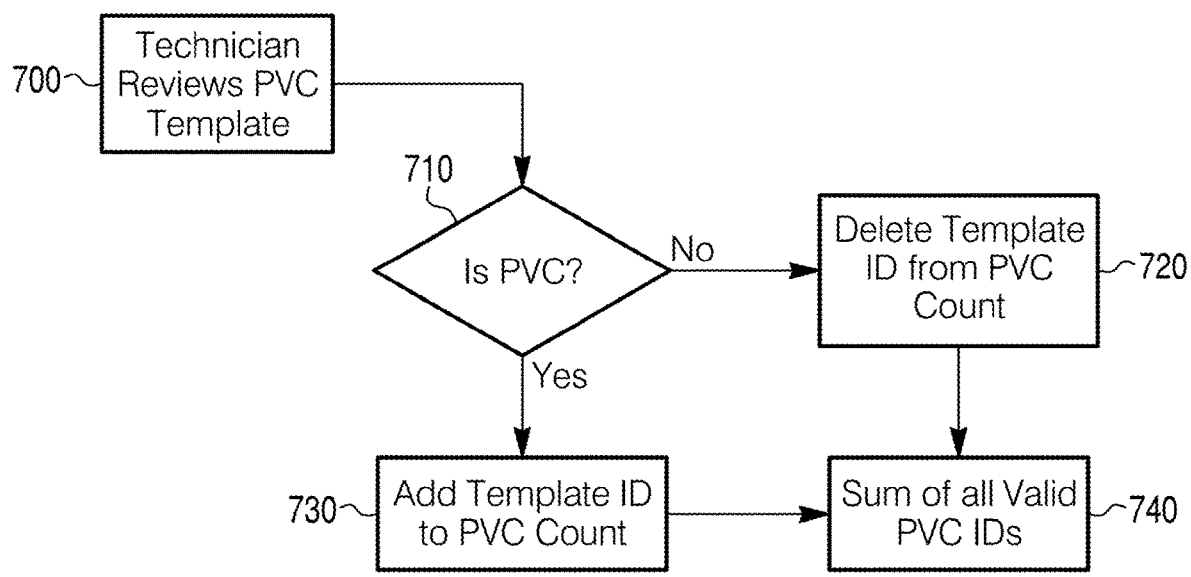

FIGS. 3 and 4 illustrate an automated method for processing ECG data to detect arrhythmias, or abnormal heartbeats. Although an exemplary embodiment of detecting premature ventricular contractions (PVCs) is described, the method can be used to detect any type of irregular heartbeat. The illustrated method may require less computational resources and may process ECG datasets with greater speed than existing methods of processing ECG data to detect PVCs. PVC detection may play a role in diagnosing a variety of heart conditions, including: heart attack, high blood pressure, cardiomyopathy (including congestive heart failure), disease of heart valves (such as mitral valve prolapse), hypokalemia (low blood levels of potassium), hypomagnesemia (low blood levels of magnesium), and hypoxia (low amounts of oxygen in the blood). In addition, several PVCs in a row with a high heart rate could indicate a serious arrhythmia, such as ventricular tachycardia.

Automatic classification of PVCs presents a challenge. For example, a patient may have over 100,000 heartbeats every day. Even if an automatic process/algorithm is 99% accurate, about 1000 beats per day may be misclassified. Time-consuming human validation may then be required to correct misclassifications. Some existing classification processes may require an entire ECG data set to be processed twice—a first processing to detect suspected PVCs and a second processing after receiving user input related to the suspected PVCs.

A method for detecting and classifying PVCs may include receiving ECG input/data. In one example, the original ECG data may be sampled at 1024 samples per second, although any other sampling rate may be used (e.g., 2048, 512, 256, etc.). The ECG input may undergo appropriate filtering and processing steps to, for example, eliminate noise; reduce the data to a lower number of samples per second, such as 200 or 100; and/or detect the amplitudes and/or thresholds of beats. This information may be used to detect PVCs. For example, PVC beats may have a higher amplitude than normal beats, and beats may be classified as PVC if they have a threshold over a fixed reference threshold.

Detected heartbeats may be labeled or classified as either: a) normal, or b) PVC. The PVC beats may be provided with a PVC template ID corresponding to their morphology (e.g., the duration and amplitude of the various waves/intervals/complexes). A PVC "template" is, for example, a representation of a suspected PVC beat that is derived from (e.g., is an average of) the characteristics of a plurality of suspected PVC beats having a similar morphology. Each template may therefore be associated with a plurality of beats having a certain morphology. Each template may have a unique template ID. Each patient 10 may have a plurality of different PVC templates, with each template corresponding to beats having a certain morphology.

FIG. 3 illustrates an exemplary method for determining whether to create a new PVC template. The method begins at step 600 with a suspected PVC beat that was detected, as described above. In step 610, the morphology of the suspected PVC may be compared to stored, previously-existing PVC templates (if there are any) to determine whether a template for the suspected PVC is known. The previously-existing PVC templates may be templates that were developed from earlier-processed heartbeats from the same patient. Additionally or alternatively, the previously-existing PVC templates may be based on known morphologies of PVCs, based on, for example, a population of patients. If the difference between the suspected PVC and the existing templates is above a certain threshold, a new PVC template may be created for the suspected PVC (step 620). In one example, the threshold may be 5% in absolute differences between one or more of the characteristics that define the morphology of a heartbeat (e.g., the duration and amplitude of the various waves/intervals/complexes). However, if the morphology of the suspected PVC is similar to an existing template (e.g., below a certain threshold), the PVC beat may be added to the existing template (step 630). In step 640, the templates are sent to a user for review.

FIG. 4 illustrates a method for user review of PVC templates. In step 700, the user reviews a PVC template. The user then determines whether the template is a PVC (step 710) and provides input to the hardware/software that analyzes the ECG data to determine arrhythmias. In one example, the user may complete step 710 by reviewing the information from the template, such as the duration and amplitude of various waves/intervals/complexes (e.g., the QRS complex), and determining whether the heartbeat is irregular when compared to the patient's normal heartbeat. Additionally or alternatively, the user might compare the information from the template to other known information about irregular heartbeats. If the user determines that the template does not represent a PVC, the template ID may be deleted from the PVC count (step 720), along with all beats associated with that template ID. Furthermore, the labels associated with each heartbeat corresponding to the deleted PVC template may be updated to indicate that the heartbeats are not PVCs. However, if the user determines that the template does represent a PVC, the template ID may be added to the PVC count (step 730). In other words, if the template ID is confirmed as a PVC by the user, all beats associated with the template ID may be confirmed and added to the PVC count, and the labels associated with each confirmed heartbeat may be updated to indicate that the heartbeats are PVCs. The beats associated with all of the valid PVC template IDs may then be added to determine the total PVC count.

Accordingly, the ECG data may be processed once to detect potential PVCs. The remaining steps of the PVC processing method may then rely on the beat labels (e.g., normal or PVC with a template ID), which may be about 200 times smaller in data size compared to the original ECG data. Because the process of FIG. 4 relies on beat labels and eliminates the need for all of the ECG data to be reprocessed to classify and total PVCs based on the user's input, the process can be carried out more efficiently than previously existing classification methods.

At the end of a pre-defined interval (e.g., a day), the total number of PVC beats may be calculated. In one example, if the total number is more than a predefined threshold (e.g., 100), the PVC statistics may be displayed by one or more of the monitor 20 or by a device used by the clinician for review.

While principles of the present disclosure are described herein with reference to illustrative embodiments for particular applications, it should be understood that the disclosure is not limited thereto. Those having ordinary skill in the art and access to the teachings provided herein will recognize additional modifications, applications, embodiments, and substitution of equivalents all fall within the scope of the embodiments described herein. Accordingly, the invention is not to be considered as limited by the foregoing description.

We claim:

1. A computer-implemented method for classifying ECG data, comprising:
   classifying, using at least one processor, heartbeats in ECG data as (i) normal heartbeats, (ii) abnormal heartbeats associated with one or more preexisting templates, or (iii) abnormal heartbeats associated with one or more new templates;
   receiving user input related to each new template of the one or more new templates after the classifying step, wherein the input includes either (a) a confirmation that the new template represents an abnormal heartbeat, (b) a reclassification of the new template as a normal heartbeat, or (c) a reclassification of the new template as representing an abnormal heartbeat different than the abnormal heartbeat from the classifying step; and
   after receiving the user input, determining, by the at least one processor, a total number of abnormal heartbeats as a sum of the heartbeats associated with (d) the one or more preexisting templates and (e) the one or more new templates representing an abnormal heartbeat.

2. The method of claim 1, wherein the method does not include repeating the classifying step between the step of receiving user input and the step of determining the total number of abnormal heartbeats.

3. The method of claim 1, wherein the classifying step includes comparing each heartbeat in the ECG data to at least one of the one or more preexisting templates.

4. The method of claim 3, wherein the classifying step further includes creating a new template of the one or more new templates if a characteristic of an abnormal heartbeat in the ECG data differs from the characteristic of each preexisting template of the one or more preexisting templates.

5. The method of claim 1, further including receiving the ECG data.

6. The method of claim 5, wherein the receiving step includes wirelessly receiving the ECG data from a portable device configured to be carried on a patient's body.

7. The method of claim 1, wherein the abnormal heartbeats represent arrhythmias.

8. The method of claim 1, wherein the abnormal heartbeats represent premature ventricular contractions.

9. The method of claim 1, further including displaying the total number of abnormal heartbeats on a display device.

10. A system for classifying ECG data, comprising:
    a data storage device that stores instructions for processing ECG data; and
    one or more processors configured to execute the instructions to perform a method including:
    classifying, using at least one processor, heartbeats in ECG data as (i) normal heartbeats, (ii) abnormal heartbeats associated with one or more preexisting templates, or (iii) abnormal heartbeats associated with one or more new templates;
    receiving user input related to each new template of the one or more new templates after the classifying step, wherein the input includes either (a) a confirmation that the new template represents an abnormal heartbeat, (b) a reclassification of the new template as a normal heartbeat, or (c) a reclassification of the new template as representing an abnormal heartbeat different than the abnormal heartbeat from the classifying step; and
    after receiving the user input, determining, by the at least one processor, a total number of abnormal heartbeats as a sum of the heartbeats associated with (d) the one or more preexisting templates and (e) the one or more new templates representing an abnormal heartbeat.

11. The system of claim 10, wherein the method performed by the one or more processors does not include repeating the classifying step between the step of receiving user input and the step of determining the total number of abnormal heartbeats.

12. The system of claim 10, wherein the classifying step includes comparing each heartbeat in the ECG data to at least one of the one or more preexisting templates.

13. The system of claim 12, wherein the classifying step further includes creating a new template of the one or more new templates if a characteristic of an abnormal heartbeat in the ECG data differs from the characteristic of each preexisting template of the one or more preexisting templates.

14. The system of claim 10, further including a wireless receiver, and the method performed by the one or more processors further includes wirelessly receiving the ECG data from a portable device configured to be carried on a patient's body.

15. The system of claim 10, wherein the abnormal heartbeats represent arrhythmias.

16. A non-transitory computer-readable medium storing instructions that, when executed by a computer, cause the computer to perform a method for classifying ECG data, the method including:
    classifying, using at least one processor, heartbeats in ECG data as (i) normal heartbeats, (ii) abnormal heartbeats associated with one or more preexisting templates, or (iii) abnormal heartbeats associated with one or more new templates;
    receiving user input related to each new template of the one or more new templates after the classifying step, wherein the input includes either (a) a confirmation that the new template represents an abnormal heartbeat, (b) a reclassification of the new template as a normal heartbeat, or (c) a reclassification of the new template as representing an abnormal heartbeat different than the abnormal heartbeat from the classifying step; and
    after receiving the user input, determining, by the at least one processor, a total number of abnormal heartbeats as a sum of the heartbeats associated with (d) the one or more preexisting templates and (e) the one or more new templates representing an abnormal heartbeat.

17. The computer-readable medium of claim 16, wherein the method does not include repeating the classifying step between the step of receiving user input and the step of determining the total number of abnormal heartbeats.

18. The computer-readable medium of claim 16, wherein the classifying step includes comparing each heartbeat in the ECG data to at least one of the one or more preexisting templates.

19. The computer-readable medium of claim 18, wherein the classifying step further includes creating a new template of the one or more new templates if a characteristic of an abnormal heartbeat in the ECG data differs from the characteristic of each preexisting template of the one or more preexisting templates.

20. The computer-readable medium of claim 16, wherein the method further includes wirelessly receiving the ECG data from a portable device configured to be carried on a patient's body.

* * * * *